(12) United States Patent
Kozasa et al.

(10) Patent No.: US 9,526,651 B2
(45) Date of Patent: Dec. 27, 2016

(54) LOWER LEG SUPPORTER

(75) Inventors: Yoshihiko Kozasa, Tokyo (JP);
Hidefumi Koga, Nara (JP)

(73) Assignee: KOWA CO., LTD. (JP)

( * ) Notice: Subject to any disclaimer, the term of this patent is extended or adjusted under 35 U.S.C. 154(b) by 145 days.

(21) Appl. No.: 13/976,883

(22) PCT Filed: Dec. 28, 2011

(86) PCT No.: PCT/JP2011/080358
§ 371 (c)(1),
(2), (4) Date: Jun. 27, 2013

(87) PCT Pub. No.: WO2012/091080
PCT Pub. Date: Jul. 5, 2012

(65) Prior Publication Data
US 2013/0281903 A1 Oct. 24, 2013

(30) Foreign Application Priority Data

Dec. 28, 2010 (JP) ................................. 2010-292843

(51) Int. Cl.
*A61F 5/01* (2006.01)
*A41D 13/05* (2006.01)
(Continued)

(52) U.S. Cl.
CPC ......... *A61F 5/0104* (2013.01); *A41D 13/0543* (2013.01); *A61F 13/08* (2013.01); *D04B 1/26* (2013.01); *D10B 2509/028* (2013.01)

(58) Field of Classification Search
CPC .... A61F 5/0104; A61F 5/0106; A61F 5/0109; A61F 13/08; A61F 13/06; A61F 13/061; A41D 13/0543; A41D 13/08; A41D 13/055; A41D 13/0556; A41D 17/00; A41D 1/08; A41D 1/082; A41D 13/0015; A41D 23/06; D04B 1/265; D04B 9/46; D04B 9/52; A41B 11/02; A41B 11/08; A43B 23/06; A63B 71/1225; A63B 2071/1258
(Continued)

(56) References Cited

U.S. PATENT DOCUMENTS 5,263,923 A  11/1993 Fujimoto

FOREIGN PATENT DOCUMENTS

FR  2958535 A1 * 10/2011
GB  413180 A  * 6/1934
(Continued)

OTHER PUBLICATIONS

JP 2002-266125 Machine Translation.*
(Continued)

*Primary Examiner* — Kari Petrik
(74) *Attorney, Agent, or Firm* — Duquette Law Group, LLC

(57) ABSTRACT

A lower leg supporter supports a gastrocnemius muscle from upper, lower, left, and right sides without interfering with movement of an Achilles tendon and which can suppress excessive vibration or deformation of such muscle to reduce a wearer's fatigue. The lower leg supporter includes a first anchor section that secures a tubular knitted fabric to a below-knee part, a second anchor section that secures the tubular knitted fabric to an above-ankle part, and an X-shaped gastrocnemius muscle support section located at a joining part of such muscle and an Achilles tendon on the back surface side of the tubular knitted fabric. Two ends of the X-shaped knitted fabric are joined to the first anchor section to support the gastrocnemius muscle. The other two ends of the X-shaped knitted fabric are joined to the second anchor section, and extend to both edges of the Achilles tendon.

12 Claims, 5 Drawing Sheets

(51) Int. Cl.
*A61F 13/08* (2006.01)
*D04B 1/26* (2006.01)

(58) Field of Classification Search
USPC .............. 2/227, 232, 22, 23, 242, 46, 228; 602/62–66
See application file for complete search history.

(56) References Cited

FOREIGN PATENT DOCUMENTS

| | | | |
|---|---|---|---|
| JP | 04-343868 | | 11/1992 |
| JP | 2002-212814 | A | 7/2002 |
| JP | 2002-266125 | A | 9/2002 |
| JP | 2002266125 | A * | 9/2002 |
| JP | 2005-256252 | A | 9/2005 |
| JP | 2007-175465 | A | 7/2007 |
| JP | 2009-150002 | A | 7/2009 |
| JP | 2010-095841 | A | 4/2010 |
| JP | 2010100981 | | 5/2010 |
| JP | 2011-021290 | A | 2/2011 |

OTHER PUBLICATIONS

FR 2958535 Machine Translation.*
Shimono, "Fundamental Manual of Surface Electromyogram", 121 pages, Nov. 1, 2004.
English translation of middle of p. 48 Cite No. 16 which corresponds to paragraph [0048] on p. 29 of the English translation of the present application.
International Search Report of International Application No. PCT/JP2011/080358 dated Feb. 21, 2012, along with English translation thereof.

* cited by examiner

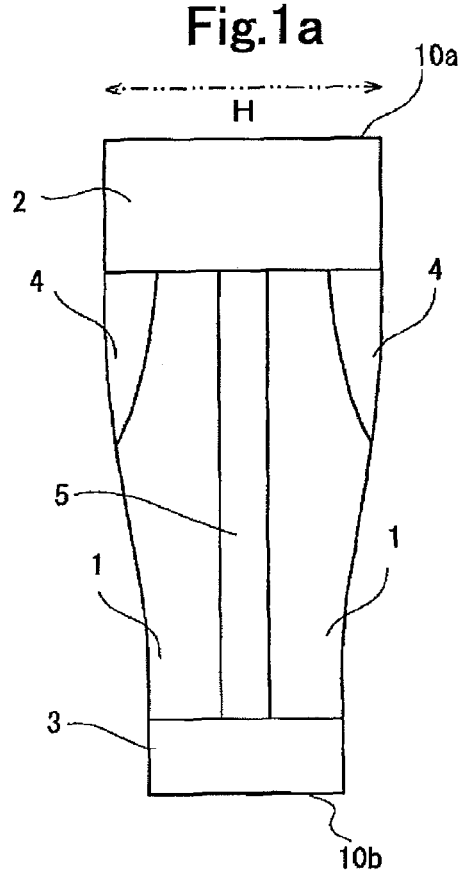
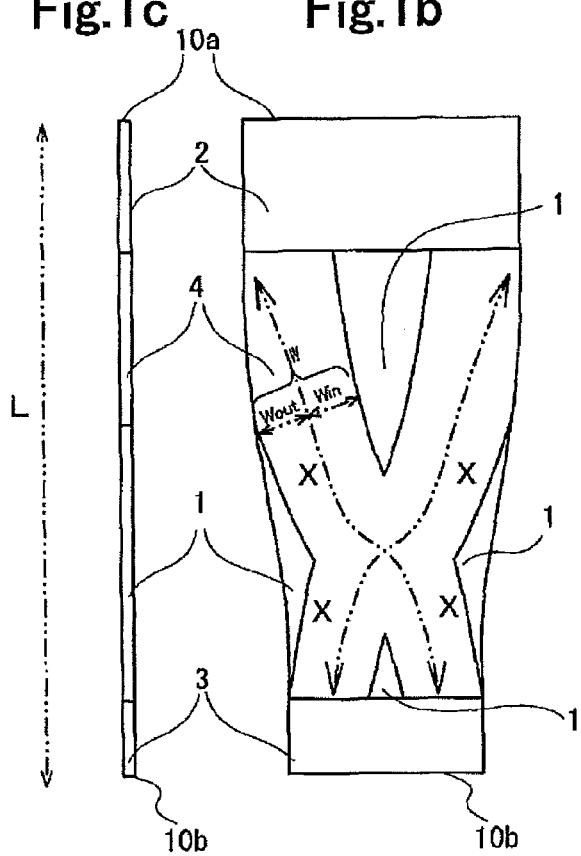

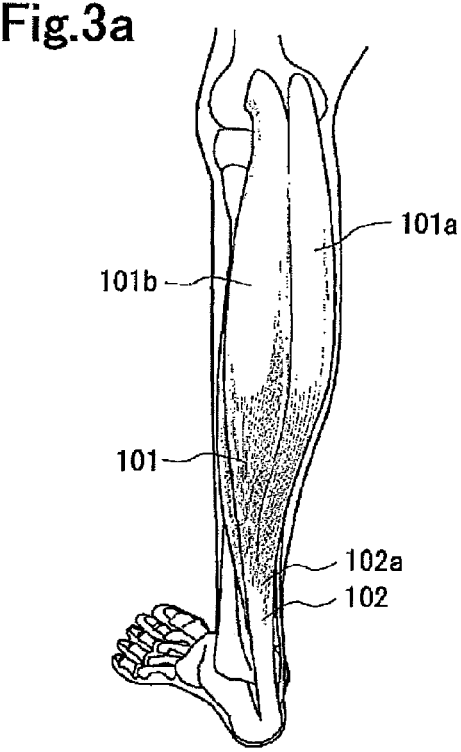
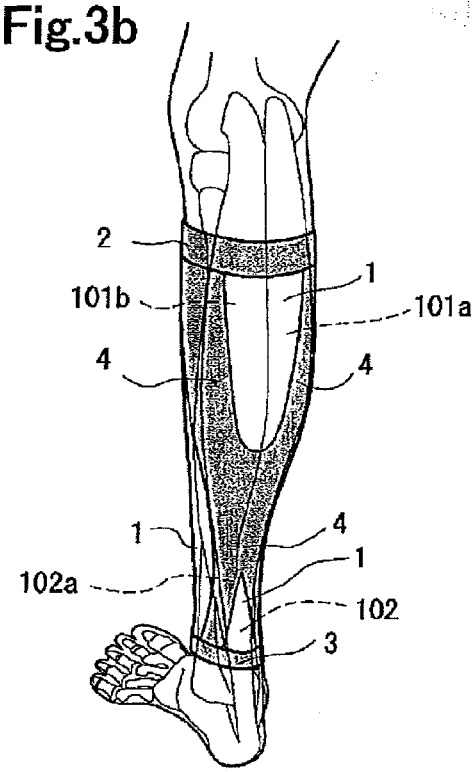
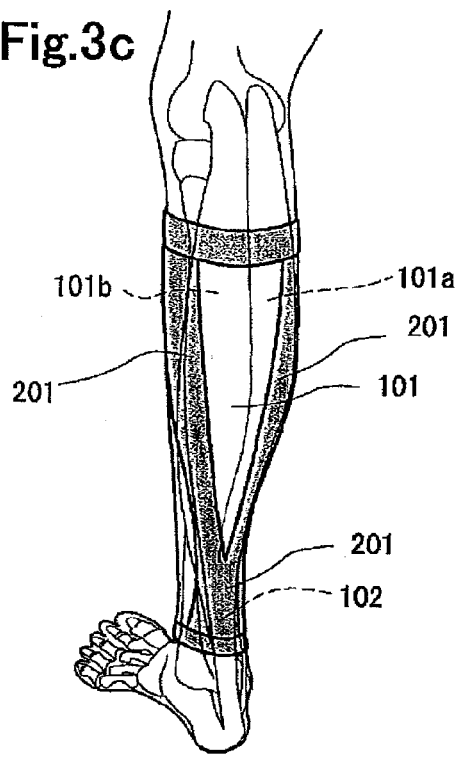

LOWER LEG SUPPORTER

TECHNICAL FIELD

The present invention relates to a lower leg supporter that can support daily motions of a wearer, and more particularly, to a lower leg supporter that has a taping function of reducing a wearer's fatigue by suppressing excessive vibration or deformation of a gastrocnemius muscle.

BACKGROUND ART

A gastrocnemius muscle is the most superficial muscle of the back surface of a lower leg, includes two capita of a caput mediale and a caput laterale, and has a so-called "calf" shape. The gastrocnemius muscle is a muscle that contributes to plantar flexion of an angle joint or flexion of a knee joint by its main movement, that extends an ankle and assists the flexion of a knee to move by standing on the tiptoe or the like by its movement in a daily life, and that strongly moves, for example, in a lot of motions including a running motion or a jumping motion.

Accordingly, when a person grows older and muscles (particularly, gastrocnemius muscle) is weakened, it is difficult to make daily motions and a calf may feel tight with fatigue in spite of occasional sports.

On the other hand, a conventional article of clothing includes a strong sheet piece having hard stretching characteristics with a strong securing force and extending substantially along a muscle fiber direction over a belly muscle from a target tendon of a human body and a weak sheet piece having soft stretching characteristics and being located in other parts not requiring securing, and is brought into close contact with the body surface of the human body so as to exhibit a taping function with the strong sheet piece (for example, see PTL 1).

A conventional calf supporter is known which includes a drum-like tube body having clamping textures at the upper and lower ends thereof and a lower part being tapered toward the end, in which the tube body has an X-suspenders reinforcing piece which is an insertion braided texture formed of a mixed fabric of nylon threads and polyurethane threads and which brings a calf portion of the tube body in close contact in the course direction, and in which the reinforcing piece is formed of a partial plating stitch texture in which knitting threads are cut at both ends (for example, see PTL 2).

A conventional calf supporter is also known in which a V-shaped lengthwise elongation suppressing texture is formed at the circumferential edge of a calf portion of the back surface, the calf portion is a portion surrounded with two lateral portions passing through the right and left side surfaces of a triceps surae muscle from an Achilles tendon and reaching the inside of a caput mediale and the outside of a caput laterale of a gastrocnemius muscle, and the lengthwise elongation suppressing texture is formed of a synthetic texture of cut-boss stitches and tuck stitches or floating stitches (for example, see PTL 3).

CITATION LIST

Patent Literature

[PTL 1] JP-A-4-343868
[PTL 2] JP-A-2002-266125
[PTL 3] JP-A-2009-150002

SUMMARY OF INVENTION

Technical Problem

In the conventional article of clothing, since the strong sheet piece is applied to pass through both sides of the gastrocnemius muscle and to cover parts of a soleus muscle and an Achilles tendon, there is a problem in that the strong sheet piece interferes with the movement of the Achilles tendon to hinder a wearer's walk.

In the conventional calf supporter, since nylon threads and polyurethane threads are mixed and knitted and a stretchable property is exhibited from the fabric in the lengthwise direction so as not to suppress stretching in the lengthwise direction, the effect of supporting the gastrocnemius muscle is not sufficiently exhibited.

In the conventional calf supporter, since the lengthwise elongation suppressing texture is located below the Achilles tendon, there is a problem in that the movement of the Achilles tendon is hindered to interfere with a wearer's walk.

Particularly, in the conventional article of clothing (calf supporter), as shown in FIG. 3(c), a strong sheet piece (the lengthwise elongation suppressing texture) 201 passes through both sides of the wearer's gastrocnemius muscle 101 (a gastrocnemius mediale 101a and a gastrocnemius laterale 101b) and is merged at a portion corresponding to the Achilles tendon 102. Accordingly, the conventional article of clothing (calf supporter) supports the gastrocnemius muscle 101 from both sides, but does not support the gastrocnemius muscle 101 from the bottom side, and the gastrocnemius muscle 101 moves vertically with the movement of the lower leg in walking or the like, whereby the effect of supporting the gastrocnemius muscle 101 is not sufficient.

The present invention is made to solve the above-mentioned problem and an object thereof is to provide a lower leg supporter which can support a gastrocnemius muscle from the lower side without interfering with movement of an Achilles tendon and which can suppress excessive vibration or deformation of the gastrocnemius muscle to reduce a wearer's fatigue.

Solution to Problem

According to the present invention, there is provided a lower leg supporter including: a first anchor section that is knitted to surround an end of the tubular knitted fabric and that secures the tubular knitted fabric to a knee part of a wearer's lower leg; a second anchor section that is knitted to surround the other end of the tubular knitted fabric and that secures the tubular knitted fabric to an ankle part of the wearer's lower leg; and a gastrocnemius muscle support section that is knitted in a substantially X-shape intersected around a portion corresponding to a joining part of a gastrocnemius muscle and an Achilles tendon of the wearer on the back side of the tubular knitted fabric, that joins two ends of the substantially X-shaped knitted fabric to the first anchor section to support the gastrocnemius muscle of the wearer, that joins the other two ends of the substantially X-shaped knitted fabric to the second anchor section, and that extends to portions corresponding to both edges of the Achilles tendon of the wearer.

Advantageous Effects of Invention

In the lower leg supporter according to the present invention, a portion corresponding to the gastrocnemius muscle of the wearer is a basic fabric, and it is possible to guarantee safety so as for the gastrocnemius muscle not to excessively move from side to side and to reduce the wearer's fatigue without interfering with the movement of the gastrocnemius muscle, by pinching the gastrocnemius muscle from the lower side by the use of the gastrocnemius muscle support section. In the lower leg supporter according to the present invention, since the gastrocnemius muscle support section is intersected around the portion corresponding to the joining part of the gastrocnemius muscle and the Achilles tendon of the wearer and is joined to the second anchor section, it is possible to suppress shifts on the upper side, the lower side, the right side, and the left side of the gastrocnemius muscle and to prevent a positional shift of the gastrocnemius muscle support section from the gastrocnemius muscle of the wearer, thereby securing the gastrocnemius muscle support section to an appropriate position. In the lower leg supporter according to the present invention, since the portion corresponding to the Achilles tendon of the wearer is a stretchable base fabric, it is possible to guarantee the degree of freedom in movement of the lower leg without causing the gastrocnemius muscle support section to press the Achilles tendon. In addition, since the elongation of the second anchor section in the circumferential direction of the tubular knitted fabric is not suppressed, it is possible to easily mount the supporter.

BRIEF DESCRIPTION OF DRAWINGS

FIG. 1(a) is a front view schematically illustrating a configuration of a lower leg supporter according to a first embodiment, FIG. 1(b) is a rear view of the lower leg supporter shown in FIG. 1(a), FIG. 1(c) is a left side view and a right side view of the lower leg supporter shown in FIG. 1(a), FIG. 1(d) is a plan view of the lower leg supporter shown in FIG. 1(a), and FIG. 1(e) is a bottom view of the lower leg supporter shown in FIG. 1(a).

FIG. 3(a) is a rear view of a human body illustrating muscle names of a lower leg, FIG. 3(b) is a diagram illustrating a wearing state of the lower leg supporter shown in FIG. 1 with reference to the view of a human body shown in FIG. 3(a), and FIG. 3(c) is a diagram illustrating the wearing state of a conventional article of clothing (calf supporter) with reference to the view of a human body shown in FIG. 3(a).

DESCRIPTION OF EMBODIMENTS (First Embodiment of the Invention)

Figure 2A:
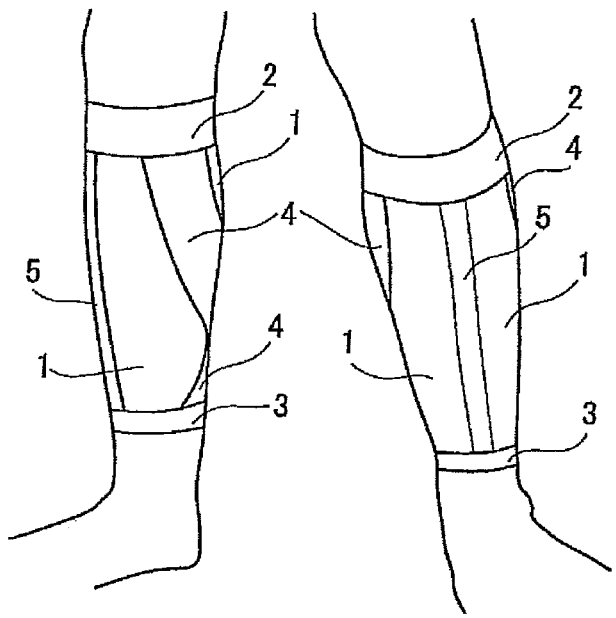
FIG. 2(a) is a perspective view illustrating a wearing state of the lower leg supporter shown in FIG. 1
Figure 2B:
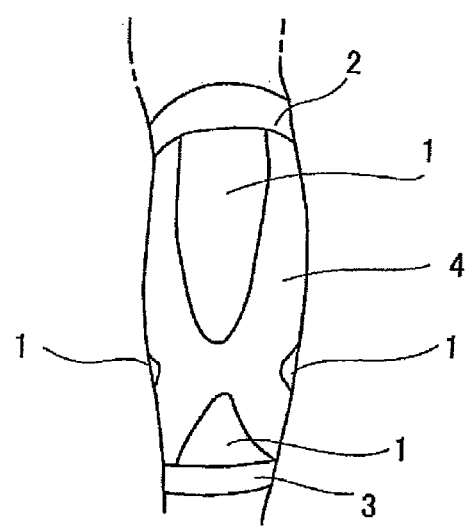
FIG. 2(b) is a rear view illustrating the wearing state of the lower leg supporter shown in FIG. 1.

In FIGS. 1 and 2, a lower leg supporter 10 is a supporter that is formed of a tubular knitted fabric knitted by round knitting using a hosiery knitting machine (for example, a knitting machine type (with the number of needles of 256) made by Lonati S.p.A.) and that comes in close contact with a wearer's body surface to support a gastrocnemius muscle of a wearer.

The lower leg supporter 10 has a desired function such as a taping function by performing different knitting operations on a base fabric section 1 which is a stretchable knitted fabric knitted with a plain stitch, a rib stitch, a tuck stitch, a float stitch or a pile stitch, and the like using a front thread, a back-side thread, and a rubber thread as a knitting thread. The base fabric section 1 according to this embodiment is a knitted fabric (hereinafter, referred to as rib-stitched fabric) knitted with a rib stitch, and stretching resistance in the length direction L of the lower leg supporter 10 is comparatively larger than the stretching resistance in the circumferential direction H of the lower leg supporter 10.

The lower leg supporter 10 includes a first anchor section 2 that is knitted to surround an end (an upper end 10a) of a tubular knitted fabric and that secures the lower leg supporter 10 to a knee part (for example, a below-knee part not overlapping with a knee) of a wearer's lower leg and a second anchor section 3 that is knitted to surround the other end (a lower end 10b) of the tubular knitted fabric and that secures the lower leg supporter 10 to an ankle part (for example, an above-ankle part not overlapping with an ankle bone) of the wear's lower leg.

The first anchor section 2 and the second anchor section 3 are knitted so that the stretching resistance in the circumferential direction H of the lower leg supporter (tubular knitted fabric) is larger than the stretching resistance of the base fabric section 1 in the circumferential direction H of the lower leg supporter 10. That is, when a tension applied to a material in a state where a tension is not applied thereto is defined F, a tension of the base fabric section 1 in the circumferential direction H of the lower leg supporter 10 is defined as $F_{H1}$, a tension of the first anchor section 2 in the circumferential direction H of the lower leg supporter 10 is defined as $F_{H2}$, and a tension of the second anchor section 3 in the circumferential direction H of the lower leg supporter 10 is defined as $F_{H3}$, a magnitude relationship of $F_{H2} \approx F_{H3} > F_{H1}$ is satisfied which represents that the first anchor section 2 and the second anchor section 3 have a stronger securing force (tightening force) in the circumferential direction H of the lower leg supporter 10 as compared to the base fabric section 1.

Specifically, by forming the first anchor section 2 and the second anchor section 3 out of a knitted fabric (hereinafter, referred to as moss-stitched fabric) knitted by a moss stitch, the stretching resistance in the circumferential direction H of the lower leg supporter 10 can be set to be larger than that of the base fabric section 1 of the rib-stitched fabric.

The moss-stitched fabric is a knitted fabric in which a plain stitch and a tuck stitch (a texture in which a knitting stitch does not depart in any course and plural loops depart in a subsequent course) appear alternately or every several courses in the course direction and the wale direction. Accordingly, by using the plain stitch and the tuck stitch together for the first anchor section 2 and the second anchor section 3, protrusion or lace stitches can be formed on the surface of a knitted fabric and thus a mesh pattern such as a moss stitch appears.

In this way, since the first anchor section 2 is knitted to surround a below-knee part of the wearer and the stretching resistance in the circumferential direction H of the lower leg supporter 10 is larger than the stretching resistance of the base fabric section 1 in the circumferential direction H of the lower leg supporter 10, it is possible to fix the lower leg supporter 10 to the below-knee part of the wearer and thus to prevent the upper end 10a of the lower leg supporter 10 from slipping down. The first anchor section 2 is joined to a gastrocnemius muscle support section 4 to be described later and also serves as an anchor of the gastrocnemius muscle support section 4.

Since the second anchor section 3 is knitted to surround the above-ankle part of the wearer and the stretching resistance in the circumferential direction H of the lower leg supporter 10 is larger than the stretching resistance of the base fabric section 1 in the circumferential direction H of the lower leg supporter 10, it is possible to fix the lower leg supporter 10 to the above-ankle part of the wearer and thus to prevent the lower end 10b of the lower leg supporter 10 from creeping up. The second anchor section 3 comes in contact with a part corresponding to the Achilles tendon of the wearer, but the knitted fabric of the second anchor section 3 has high elasticity, thereby being able to alleviate impact on the Achilles tendon. The second anchor section 3 is joined to a gastrocnemius muscle support section 4 to be described later and also serves as an anchor of the gastrocnemius muscle support section 4.

When the securing force (tightening force) of the first anchor section 2 and the second anchor section 3 to the below-knee part and the above-ankle part of the wearer is excessively strong, interruption of blood supply is caused in the below-knee part and the above-ankle part, thereby giving an uncomfortable feeling to the wearer. Particularly, this uncomfortable feeling is more marked in the below-knee part than in the above-ankle part.

Accordingly, in the lower leg supporter 10 according to this embodiment, by adjusting the stitches in a part of the first anchor section 2 (for example, reducing the securing force (tightening force) to be smaller by about 10% than that of the second anchor section 3), the uncomfortable feeling given to the wearer is alleviated and the inroad into the skin is suppressed. That is, it is preferable that the lower leg supporter 10 according to this embodiment satisfy the magnitude relationship of $F_{H3} > F_{H2} > F_{H1}$ so as to have an appropriate securing force (tightening force) in the circumferential direction H of the lower leg supporter 10. In the lower leg supporter 10 according to this embodiment, the pressure applied to the body surface of the wearer from the first anchor section 2 is set to be smaller than the pressure (pressing force per unit area) applied to the body surface of the wearer from the second anchor section 3, but it is possible to obtain a desired securing force (tightening force) as a whole by increasing the width in the length direction L of the first anchor section 2 than the second anchor section 3, thereby suppressing the slipping-down of the upper end 10a of the lower leg supporter 10.

As shown in FIG. 3, the gastrocnemius muscle support section 4 is disposed on the rear surface of the lower leg supporter 10, is knitted in a substantially X-shape intersected around the portion corresponding to a joining part 102a of the gastrocnemius muscle 101 and the Achilles tendon 102 of the wearer, and joins two ends of the substantially X-shaped knitted fabric to the first anchor section 2 to support the gastrocnemius muscle 101 of the wearer from the upper, lower, right, and left sides. The gastrocnemius muscle support section 4 joins the other two ends of the substantially X-shaped knitted fabric to the second anchor section 3 and extends to the portions of both edges of the Achilles tendon 102 of the wearer to avoid the portion corresponding to the Achilles tendon 102 of the wearer. That is, the gastrocnemius muscle support section 4 is locked to the first anchor section 2 in the knee part of the wearer and is locked to the second anchor section 3 in the above-ankle part of the wearer.

As shown in FIG. 1(b) and FIG. 3(b), the gastrocnemius muscle support section 4 has such a width W (the inside width $W_{in}$ and the outside width $W_{out}$) to surround a part of the gastrocnemius muscle 101 and the periphery thereof from the outer edge of the gastrocnemius muscle 101 in the portions corresponding to the gastrocnemius muscle 101 (the gastrocnemius mediale 101a and the gastrocnemius laterale 101b) of the wearer.

Particularly, when the inside width $W_{in}$ of the gastrocnemius muscle support section 4 is excessively large, the movement of the gastrocnemius muscle 101 is hindered, and it is thus preferable that the inside width $W_{in}$ has such a value not to hinder the movement of the gastrocnemius muscle 101.

The gastrocnemius muscle support section 4 is preferably formed so that the stretching resistance in the length direction (direction X extending along the curve (see FIG. 1(b))) of the gastrocnemius muscle support section 4 is larger than the stretching resistance in the widthwise direction W (direction perpendicular to the extending direction X) of the gastrocnemius muscle support section 4, but it is difficult to knit a knitted fabric having this difference in stretching resistance by the round knitting. Therefore, in this embodiment, the gastrocnemius muscle support section 4 in which the stretching resistance in the length direction L of the lower leg supporter 10 is larger than the stretching resistance in the circumferential direction H of the lower leg supporter 10 is formed to approximate a knitted fabric having the difference in stretching resistance.

The gastrocnemius muscle support section 4 is knitted so that the stretching resistance in the length direction L of the lower leg supporter 10 is larger than the stretching resistance of the base fabric section 1 in the length direction L of the lower leg supporter 10. That is, when the tension of the base fabric section 1 in the length direction L of the lower leg supporter 10 is defined as $F_{L1}$ and the tension of the gastrocnemius muscle support section 4 in the length direction L of the lower leg supporter 10 is defined as $F_{L4}$, a magnitude relationship of $F_{L4} > F_{L1}$ is satisfied which represents that the gastrocnemius muscle support section 4 is larger in the securing force (tightening force) in the length direction L of the lower leg supporter 10 than the base fabric section 1.

Specifically, by forming the gastrocnemius muscle support section 4 out of a knitted fabric (hereinafter, referred to as a tuck-stitched and plating-stitched knitted fabric) using a tuck stitch and a plating stitch together, the stretching resistance in the length direction L of the lower leg supporter 10 can be set to be larger than that of the rib-stitched base fabric section 1.

The tuck-stitched knitted fabric is a knitted fabric in which a knitting stitch is not formed in a course and knitting stitches are formed together in the next course when knitting the fabric. In this embodiment, the number of tuck stitching is set to one in consideration of the balance with the stitches, but the number tuck stitching is not limited to this number.

In the tuck-stitched and plating-stitched knitted fabric, by feeding another thread (for example, woolly nylon thread) in addition to a fabric-knitting thread of a tuck stitch, the stretching of the gastrocnemius muscle support section 4 in the length direction L of the lower leg supporter 10 is appropriately suppressed and another thread is cut (cut-boss) at the boundary between the gastrocnemius muscle support section 4 and the base fabric section 1.

In this way, since the gastrocnemius muscle support section 4 is joined to the first anchor section 2 and the second anchor section 3, is knitted in the substantially X-shape to surround a part of the gastrocnemius muscle 101 of the wearer and the periphery thereof, is set so that the stretching resistance in the length direction L of the lower leg supporter 10 is larger than the stretching resistance of the circumferential direction H of the lower leg supporter 10 and is larger than the stretching resistance of the base fabric section 1 in the length direction L of the lower leg supporter 10, the following operational advantages are achieved.

By supporting the gastrocnemius muscle 101 of the wearer from the ankle side to the knee side and assisting the contraction of the gastrocnemius muscle 101, the gastrocnemius muscle support section 4 can smooth the movement of the wearer's leg, can suppress shift or deformation of the gastrocnemius muscle 101 to the upper, lower, right, and left sides to assist the wearer's walk, and can prevent loss of strength of the wearer to reduce fatigue (taping function). The gastrocnemius muscle support section 4 can suppress shift of the wearer's lower leg by the use of the intersection portion corresponding to the joining part 102a of the gastrocnemius muscle 101 and the Achilles tendon 102 of the wearer.

The specially-functional knitted fabric (tuck-stitched and plating-stitched knitted fabric) in the gastrocnemius muscle support section 4 is joined to the moss-stitched fabric in the first anchor section 2 and the second anchor section 3, thereby preventing the positional shift of the gastrocnemius muscle support section 4 from the gastrocnemius muscle 101 of the wearer and fixing the gastrocnemius muscle support section 4 to an appropriate position.

Since the gastrocnemius muscle support section 4 avoids the portion corresponding to the Achilles tendon 102 of the wearer (the portion corresponding to the Achilles tendon 102 is the basic fabric 1), it is possible to secure the degree of freedom in movement of the lower leg without causing the gastrocnemius muscle support section 4 to press the Achilles tendon 102. Moreover, since the elongation of the second anchor section 3 in the circumferential direction H of the lower leg supporter 10 is not suppressed, it is possible to easily mount the lower leg supporter 10.

Particularly, the fabric of the gastrocnemius muscle support section 4 is thicker than the base fabric section 1 adjacent to the gastrocnemius muscle support section 4 due to the plating-stitched fabric (cut-boss) based on the addition of another knitting thread to the fabric-knitting thread, a step difference is formed at the boundary with the base fabric section 1, and it is thus possible to give the wearer such an actual feeling that the gastrocnemius muscle 101 of the wearer is supported by the gastrocnemius muscle support section 4.

When it is intended to form the step difference at the boundary between the gastrocnemius muscle support section 4 and the base fabric section 1, a liquid resin may be applied to the boundary between the gastrocnemius muscle support section 4 and the base fabric section 1 so as to oxidize the resin by contact with air to be adhesive, a thin-film-like resin may be bonded, or a liquid resin may be sprayed with a sprayer so as to oxidize the resin by contact with air to be adhesive. By applying an adhesive resin formed of resins such as polyesters, polyamides, polyurethanes, polyethylenes (with a high density or a low density), or ethylene vinyl acetates to the boundary between the gastrocnemius muscle support section 4 and the base fabric section 1 through the use of a processing method such as dot processing, powder processing, cobweb processing, or film processing and heating and pressurizing the adhesive resin through the use of a flat-type press machine or a roller-type press machine, or the like, a resin may be adhered to the knitted fabric.

An anterior tibial muscle support section 5 is a section which is knitted in a substantially straight line shape between the first anchor section 2 and the second anchor section 3 substantially at the center of the front surface of the lower leg supporter 10 and which supports an anterior tibial muscle of the wearer, and is knitted so that the stretching resistance in the length direction L of the lower leg supporter 10 is larger than the stretching resistance in the circumferential direction H of the lower leg supporter 10.

The anterior tibial muscle support section 5 is knitted so that the stretching resistance in the length direction L of the lower leg supporter 10 is larger than the stretching resistance of the base fabric section 1 in the length direction L of the lower leg supporter 10 and is smaller than the stretching resistance of the gastrocnemius muscle support section 4 in the length direction L of the lower leg supporter 10. That is, when the tension of the anterior tibial muscle support section 5 in the length direction L of the lower leg supporter 10 is defined as $F_{L5}$, a magnitude relationship of $F_{L4} > F_{L5} > F_{L1}$ is satisfied which represents that the anterior tibial muscle support section 5 has a larger securing force (tightening force) in the length direction L of the lower leg supporter 10 than the base fabric section 1 and the anterior tibial muscle support section 5 has a smaller securing force (tightening force) in the length direction L of the lower leg supporter 10 than the gastrocnemius muscle support section 4.

Specifically, by forming the anterior tibial muscle support section 5 out of a tuck-stitched knitted fabric, the stretching resistance in the length direction L of the lower leg supporter 10 can be set to be larger than that of the base fabric section 1 formed of a rib-stitched knitted fabric and to be smaller than the stretching resistance of the gastrocnemius muscle support section 4, which is formed of a tuck-stitched and plating-stitched knitted fabric, in the length direction L of the lower leg supporter 10.

In this way, since the anterior tibial muscle support section 5 corresponds to the anterior tibial muscle of the wearer and the stretching resistance in the length direction L of the lower leg supporter 10 is larger than the stretching resistance of the base fabric section 1 in the length direction L of the lower leg supporter 10 and is smaller than the stretching resistance of the gastrocnemius muscle support section 4 in the length direction L of the lower leg supporter 10, it is possible to assist the function of the anterior tibial muscle and to alleviate a pain due to the pressing of the lower leg supporter 10 against the tibial bone. Since the anterior tibial muscle support section 5 is knitted in a substantially straight line shape between the first anchor section 2 and the second anchor section 3 substantially at the center of the front surface of the lower leg supporter 10, the anterior tibial muscle support section serves as a mark for securing the lower leg supporter 10 to a correct position.

In this embodiment, the front thread formed of a woolly nylon thread with a thickness of 70 deniers and having two pieces of knitting, the back-side thread formed of a woolly nylon thread with a thickness of 30 deniers and having two pieces of knitting, and the rubber thread which is a double-covered yarn (DCY) in which two nylon wound yarns with a thickness of 40 deniers are wound on a polyurethane core thread with a thickness of 260 deniers are used as the fabric-knitting thread used for a rib stitch and a tuck stitch in the body fabric (the base fabric section 1, the gastrocnemius muscle support section 4, and the anterior tibial muscle support section 5), but the fabric-knitting thread is not limited to this material.

In this embodiment, the front thread formed of a woolly nylon thread with a thickness of 70 deniers and having two pieces of knitting and the back-side thread formed of a woolly nylon thread with a thickness of 30 deniers and having two pieces of knitting are used as the fabric-knitting thread used for a moss stitch in the rib top section (the first anchor section 2 and the second anchor section 3), but the fabric-knitting thread is not limited to this material.

For example, it is preferable that natural fibers such as cotton, fur (such as cashmere, lamb, or angora), silk, or hemp, chemical fibers such as acrylic, or materials having a sweat-absorbing, quick-drying, or thermo-regulating function be selected as the front thread depending on the cost of the lower leg supporter 10 or the wearer's request. It is preferable that ester or FTY (Filament Twisted Yarn) or antimicrobial, odor-resistant, or deodorant materials be selected as the back-side thread depending on the cost of the lower leg supporter 10 or the wearer's request.

The woolly nylon thread (patterning thread) in the tuck-stitched and plating-stitched knitted fabric (the gastrocnemius muscle support section 4) includes two pieces of knitting with a thickness of 70 deniers.

The lower leg supporter 10 may additionally have a warming function, for example, using a moisture-absorbing and heat-generating material, a far-infrared material, a photoelectron material, a mineral-tempered material, or a thermal storage material, as the front thread and/or the back-side thread. On the contrary, the lower leg supporter 10 may additionally have a cooling function, for example, using a contact cold-sensation material, a water-absorbing and quick-drying material, a heat-absorbing or heat-dissipating material, or a cool processed material as the front thread and/or the back-side thread.

By using a colored knitting thread (for example, a patterning thread of blue or pink) as the front thread and/or the back-side thread, the lower leg supporter 10 may cause a consumer to visually feel a sense of beauty, thereby achieving distinction from the conventional white supporter to enhance purchasing needs.

Figure 4A:
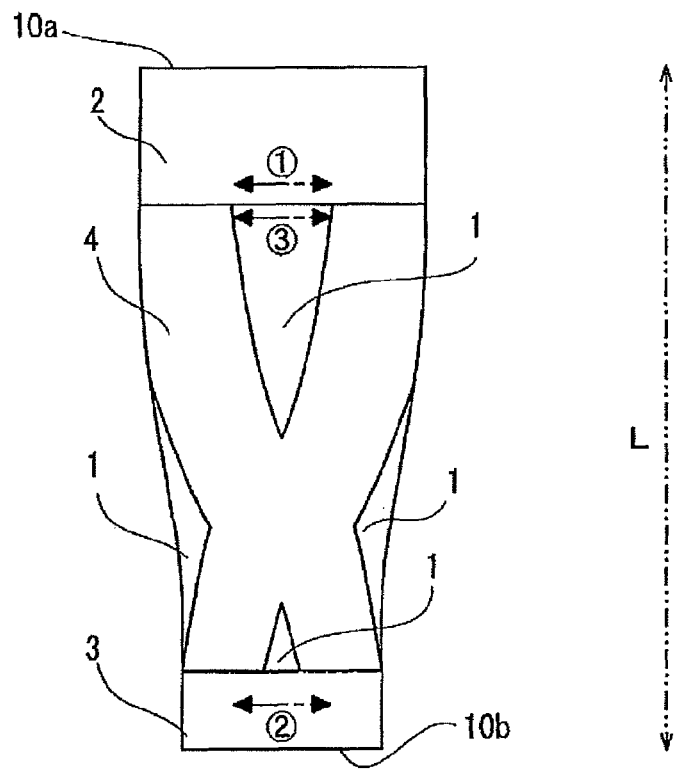
FIG. 4(a) is a diagram illustrating a part of which an elongation rate is measured in the lower leg supporter shown in FIG. 1
Figure 4B:
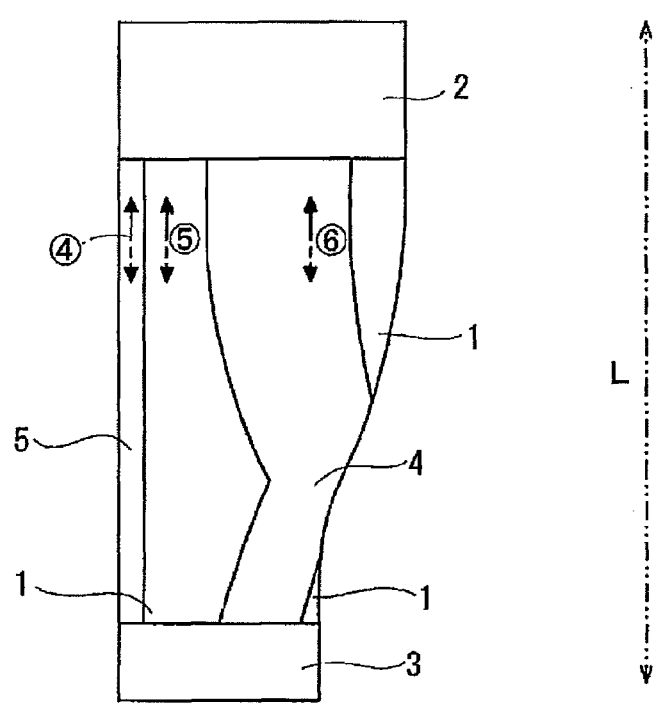
FIG. 4(b) is another diagram illustrating the part of which an elongation rate is measured in the lower leg supporter shown in FIG. 1.

Here, the magnitude of stretching resistance of the lower leg supporter 10 manufactured using the above-mentioned knitting threads and the knitted fabrics was checked. In the checking method, the stretching rates (percentage ratio of a difference between the stretched length (stretched size) and the original length (original size) to the original length) of the portions (see FIG. 4) of the lower leg supporter 10 were measured by the sue of a stretch tester (with a tensile load of 4 kg). The result is shown in Table 1.

TABLE 1

| Measured portions | | Original size [cm] | Stretched size [cm] | Stretching rate [%] |
|---|---|---|---|---|
| Round number 1 | Circumferential direction H of first anchor section 2 | 6.0 | 20.0 | 233.3 |
| Round number 2 | Circumferential direction H of second anchor section 3 | 6.0 | 19.0 | 216.7 |
| Round number 3 | Circumferential direction H of base fabric section 1 | 6.0 | 21.0 | 250.0 |
| Round number 4 | Length direction L of anterior tibial muscle support section 5 | 8.0 | 19.0 | 137.5 |
| Round number 5 | Length direction L of base fabric section 1 | 8.0 | 20.0 | 150.0 |
| Round number 6 | Length direction L of gastrocnemius muscle support section 4 | 8.0 | 15.0 | 87.5 |

The original sizes shown in Table 1 are only examples of the lower leg supporter 10, and the lower leg supporter 10 is not limited to the sizes. Changes or modifications based on the knowledge of a person skilled in the art without departing from the concept of the present invention belong to the scope of the present invention. The stretching rate in Table 1 represents that as the larger the value is, the more easily the knitted fabric is stretched, but the tension F represents that the larger the tension F is, the more difficultly the knitted fabric is stretched (the larger the securing force (tightening force) is). Accordingly, the magnitude relationship of the stretching rate is opposite to the magnitude relationship of the tension F.

In Table 1, it was confirmed that the lower leg supporter 10 has the above-mentioned relationships of $F_{H3} > F_{H2} > F_{H1}$ and $F_{L4} > F_{L5} > F_{L1}$.

The verification result of the operational advantages of the lower leg supporter 10 according to this embodiment will be described below.

In the test, when the lower leg supporter 10 according to the present invention is mounted on the right calf of a test subject (normal adult male of 175 cm/70 kg who is 27 years old) (wearing state) and when the lower leg supporter 10 is not mounted thereon (non-wearing state), the test subject performed standing on his tiptoe with a load of 50% kept on the right and left legs up to the limit, and then the frequency in the surface electromyogram of the gastrocnemius muscle of the test subject was analyzed through the use of a surface electromyograph. "Myoresearch Xp" made by Noraxon U.S.A. Inc. was used as the surface electromyography and the result is shown in FIG. 5.

In general, it is considered that the frequency in the surface electromyogram is lowered due to muscle fatigue (the waveform is changed to a slow waveform). This is based on factors such as a decrease in discharge frequency of motion units, a decrease in power transmission rate of muscle fibers, and an increase in synchronization of motion units (see a publication name of "Fundamental Manual of Surface Electromyogram", written by Toshiya SHIMONO, issued by SAKAI Medical. Co., Ltd.).

Figure 5:
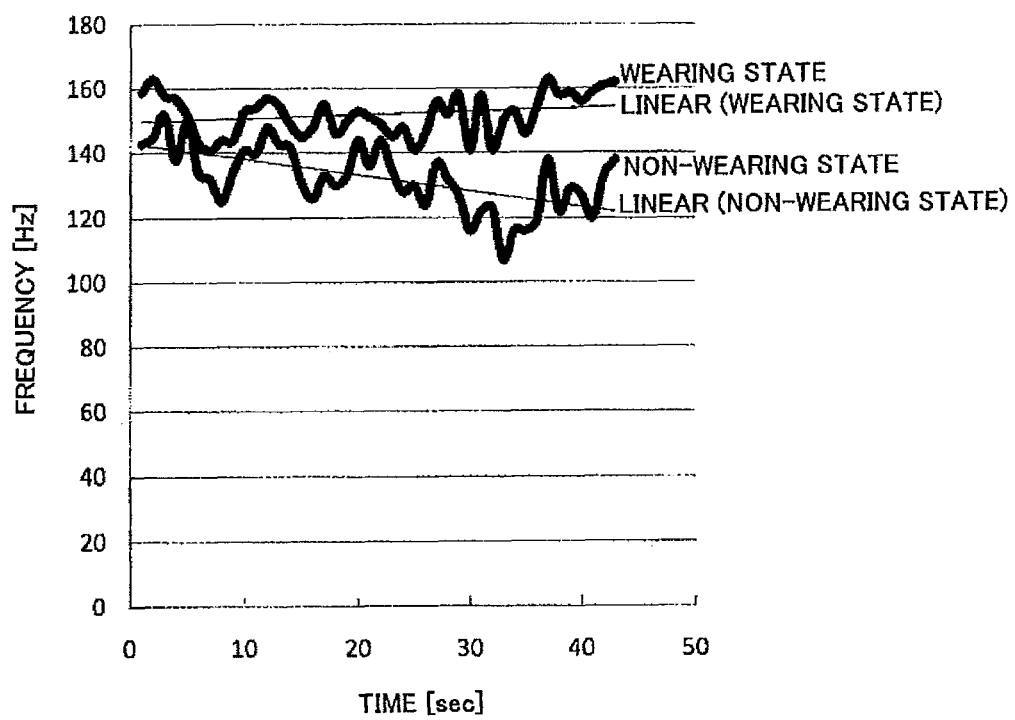
FIG. 5 is a surface electromyogram used to verify the operational advantages of the lower leg supporter shown in FIG. 1.

As shown in FIG. 5, since the frequency (linear) in the non-wearing state is lowered with the lapse of time, but the frequency (linear) in the wearing state hardly vary, it is apparent that the lower leg supporter 10 contributes to prevention of a wearer's muscle fatigue by assisting the gastrocnemius muscle with appropriate tightening.

Reference Signs List

1: BASE FABRIC SECTION
2: FIRST ANCHOR SECTION
3: SECOND ANCHOR SECTION
4: GASTROCNEMIUS MUSCLE SUPPORT SECTION
5: ANTERIOR TIBIAL MUSCLE SUPPORT SECTION
10: LOWER LEG SUPPORTER
10a: UPPER END
10b: LOWER END
101: GASTROCNEMIUS MUSCLE
101a: GASTROCNEMIUS MEDIALE MUSCLE
101b: GASTROCNEMIUS LATERALE MUSCLE
102: ACHILLES TENDON
102a: JOINING PART
201: STRONG SHEET PIECE (LENGTHWISE ELONGATION SUPPRESSING TEXTURE)
H: CIRCUMFERENTIAL DIRECTION
L: LENGTH DIRECTION
W: WIDTH
$W_{in}$: INSIDE WIDTH
$W_{out}$: OUTSIDE WIDTH
X: LENGTH DIRECTION OF GASTROCNEMIUS MUSCLE SUPPORT SECTION

The invention claimed is:

1. A lower leg supporter constructed from a tubular knitted fabric knitted by rounding knitting and that is adapted to come in close contact with a wearer's body surface to assist the wearer's gastrocnemius muscle, comprising:
a first anchor section that is knitted around a first end of the tubular knitted fabric knitted by rounding knitting and that is adapted to secure the tubular knitted fabric knitted by rounding knitting to a knee part of the wearer's lower leg;
a second anchor section that is knitted around a second end of the tubular knitted fabric knitted by rounding knitting and that is adapted to secure the tubular knitted fabric knitted by rounding knitting to an ankle part of the wearer's lower leg; and
a gastrocnemius muscle support section that is knitted in a substantially X-shape on a back side of the tubular knitted fabric knitted by rounding knitting, a first set of support elements of the gastrocnemius muscle support section joined to the first anchor section and a second set of support elements of the gastrocnemius muscle support section joined to the second anchor section,
wherein a base fabric section of the tubular knitted fabric knitted by rounding knitting is arranged at least in a region which is surrounded with the first anchor section and the gastrocnemius muscle support section in a portion adapted to support the gastrocnemius muscle of the wearer and in a region which is surrounded with the second anchor section and the gastrocnemius muscle support section in a portion adapted to support an Achilles tendon of the wearer, and
an intersection of the first set of support elements of the gastrocnemius muscle support section and the second set of support elements of the gastrocnemius muscle support section disposed closer to the second anchor section than to the first anchor section.

2. The lower leg supporter according to claim 1, wherein a stretching resistance of the gastrocnemius muscle support section in a length direction of the tubular knitted fabric knitted by rounding knitting is larger than a stretching resistance of the gastrocnemius muscle support section in a circumferential direction of the tubular knitted fabric knitted by rounding knitting.

3. The lower leg supporter according to claim 2, wherein the gastrocnemius muscle support section is a knitted fabric using tuck stitches and plating stitches together.

4. The lower leg supporter according to claim 2, wherein a stretching resistance of the first anchor section in the circumferential direction of the tubular knitted fabric knitted by rounding knitting is smaller than a stretching resistance of the second anchor section in the circumferential direction of the tubular knitted fabric knitted by rounding knitting and is larger than a stretching resistance of the base fabric section in the circumferential direction of the tubular knitted fabric knitted by rounding knitting.

5. The lower leg supporter according to claim 2, further comprising an anterior tibial muscle support section that is knitted in a substantially straight line shape to be joined to the first anchor section and the second anchor section between the first anchor section and the second anchor section substantially at a center of a front surface of the tubular knitted fabric knitted by rounding knitting and that is adapted to support an anterior tibial muscle of the wearer,
wherein a stretching resistance of the anterior tibial muscle support section in a length direction of the tubular knitted fabric knitted by rounding knitting is larger than a stretching resistance of the base fabric section in the length direction of the tubular knitted fabric knitted by rounding knitting and is smaller than the stretching resistance of the gastrocnemius muscle support section in the length direction of the tubular knitted fabric knitted by rounding knitting.

6. The lower leg supporter according to claim 1, wherein the gastrocnemius muscle support section is a knitted fabric using tuck stitches and plating stitches together.

7. The lower leg supporter according to claim 6, wherein a stretching resistance of the first anchor section in a circumferential direction of the tubular knitted fabric knitted by rounding knitting is smaller than a stretching resistance of the second anchor section in the circumferential direction of the tubular knitted fabric knitted by rounding knitting and is larger than a stretching resistance of the base fabric section in the circumferential direction of the tubular knitted fabric knitted by rounding knitting.

8. The lower leg supporter according to claim 6, further comprising an anterior tibial muscle support section that is knitted in a substantially straight line shape to be joined to the first anchor section and the second anchor section between the first anchor section and the second anchor section substantially at a center of a front surface of the tubular knitted fabric knitted by rounding knitting and that is adapted to support an anterior tibial muscle of the wearer,
wherein a stretching resistance of the anterior tibial muscle support section in a length direction of the tubular knitted fabric knitted by rounding knitting is larger than a stretching resistance of the base fabric section in the length direction of the tubular knitted fabric knitted by rounding knitting and is smaller than a stretching resistance of the gastrocnemius muscle support section in the length direction of the tubular knitted fabric knitted by rounding knitting.

9. The lower leg supporter according to claim 1, wherein a stretching resistance of the first anchor section in a circumferential direction of the tubular knitted fabric knitted by rounding knitting is smaller than a stretching resistance of the second anchor section in the circumferential direction of the tubular knitted fabric knitted by rounding knitting and is larger than a stretching resistance of the base fabric section in the circumferential direction of the tubular knitted fabric knitted by rounding knitting.

10. The lower leg supporter according to claim 9, further comprising an anterior tibial muscle support section that is knitted in a substantially straight line shape to be joined to the first anchor section and the second anchor section between the first anchor section and the second anchor section substantially at a center of a front surface of the tubular knitted fabric knitted by rounding knitting and that is adapted to support an anterior tibial muscle of the wearer,
wherein a stretching resistance of the anterior tibial muscle support section in a length direction of the tubular knitted fabric knitted by rounding knitting is larger than a stretching resistance of the base fabric section in the length direction of the tubular knitted fabric knitted by rounding knitting and is smaller than a stretching resistance of the gastrocnemius muscle support section in the length direction of the tubular knitted fabric knitted by rounding knitting.

11. The lower leg supporter according to claim 1, further comprising an anterior tibial muscle support section that is knitted in a substantially straight line shape to be joined to the first anchor section and the second anchor section between the first anchor section and the second anchor section substantially at a center of a front surface of the tubular knitted fabric knitted by rounding knitting and that is adapted to support an anterior tibial muscle of the wearer,
wherein a stretching resistance of the anterior tibial muscle support section in a length direction of the tubular knitted fabric knitted by rounding knitting is larger than a stretching resistance of the base fabric section in the length direction of the tubular knitted fabric knitted by rounding knitting and is smaller than a stretching resistance of the gastrocnemius muscle support section in the length direction of the tubular knitted fabric knitted by rounding knitting.

12. A lower leg supporter constructed from a tubular knitted fabric knitted by rounding knitting and that is adapted to come in close contact with a wearer's body surface to assist the wearer's gastrocnemius muscle, comprising:
a first anchor section that is knitted around a first end of the tubular knitted fabric knitted by rounding knitting and that is adapted to secure the tubular knitted fabric knitted by rounding knitting to a knee part of the wearer's lower leg;
a second anchor section that is knitted around a second end of the tubular knitted fabric knitted by rounding knitting and that is adapted to secure the tubular knitted fabric knitted by rounding knitting to an ankle part of the wearer's lower leg; and
a gastrocnemius muscle support section that is knitted in a substantially X-shape on a back side of the tubular knitted fabric knitted by rounding knitting, a first set of support elements of the gastrocnemius muscle support section joined to the first anchor section and a second set of support elements of the gastrocnemius muscle support section joined to the second anchor section,
wherein a region which is surrounded with the first anchor section and the first set of support elements of the gastrocnemius muscle support section are configured to surround only a base fabric section of the tubular knitted fabric knitted by rounding knitting arranged in a portion adapted to support the gastrocnemius muscle of the wearer,
wherein a region which is surrounded with the second anchor section and the second set of support elements of the gastrocnemius muscle support section are configured to surround only a base fabric section of the tubular knitted fabric knitted by rounding knitting arranged in a portion adapted to support an Achilles tendon of the wearer, and
an intersection of the first set of support elements of the gastrocnemius muscle support section and the second set of support elements of the gastrocnemius muscle support section disposed closer to the second anchor section than to the first anchor section.

* * * * *